(12) United States Patent
Suzuki et al.

(10) Patent No.: US 6,872,759 B2
(45) Date of Patent: Mar. 29, 2005

(54) ARTIFICIAL DURA MATER HAVING CELL ADHESIVENESS AND A PROCESS FOR PRODUCING THE SAME

(75) Inventors: Yoshiaki Suzuki, Tokyo (JP); Masaya Iwaki, Niiza (JP); Makoto Kaibara, Shiki (JP); Masami Kamio, Yokohama (JP)

(73) Assignee: Riken, Saitama (JP)

( * ) Notice: Subject to any disclaimer, the term of this patent is extended or adjusted under 35 U.S.C. 154(b) by 110 days.

(21) Appl. No.: 10/122,305

(22) Filed: Apr. 16, 2002

(65) Prior Publication Data

US 2002/0155295 A1 Oct. 24, 2002

(30) Foreign Application Priority Data

Apr. 23, 2001 (JP) .......................................... 2001-124294

(51) Int. Cl.[7] ................ C08F 2/46; C08J 3/28
(52) U.S. Cl. ................ 522/2; 522/90; 522/93; 522/100; 522/104; 522/130
(58) Field of Search ............... 522/2, 90, 93, 522/100, 104, 130

(56) References Cited

U.S. PATENT DOCUMENTS

| | | | |
|---|---|---|---|
| 5,133,757 A | 7/1992 | Sioshansi et al. | |
| 5,308,704 A | 5/1994 | Suzuki et al. | |
| 5,906,824 A | 5/1999 | Suzuki et al. | |
| 6,051,751 A | 4/2000 | Sioshansi et al. | |
| 6,217,615 B1 | 4/2001 | Sioshansi et al. | |

FOREIGN PATENT DOCUMENTS

DE     19904913     9/1999

OTHER PUBLICATIONS

M. Kusakabe et al., "Control of Endothelial Cell Adhesion to Polymer Surface by Ion Implantation", *Polymers for Advanced Technologies*, vol. 12, pp. 453–460 (2001).

Y. Suzuki et al., "Endothelial Cell Adhesion to Ion Implanted Polymers", *Nuclear Instruments and Methods in Physics Research*, B65, pp. 142–147 (1992).

English Language Abstract of DE 19904913, published Sep. 16, 1999.

Yamagata S. et al., Database Medline, Aug. 1993, "Clinical Experience with Expanded Polytetrafluoroethylene Sheet Used as an Artificial Dura Mater", Database accession No. NLM7692335, XP 002205658.

*Primary Examiner*—Nathan M. Nutter
(74) *Attorney, Agent, or Firm*—Greenblum & Bernstein, P.L.C.

(57) ABSTRACT

The present invention provides a material having adhesiveness to bone and/or fascia, which is composed of a polymeric material comprising carbon as a constituent element, and at least a part of a surface of which is modified by ion bombardment. The material of the present invention is applicable as a prosthesis in surgery of spinal diseases and as a prosthesis in surgery on thoracic organs and abdominal organs or musculoskeleton in addition to the application thereof to the artificial dura mater.

7 Claims, 4 Drawing Sheets

ARTIFICIAL DURA MATER HAVING CELL ADHESIVENESS AND A PROCESS FOR PRODUCING THE SAME

TECHNICAL FIELD

The present invention relates to a material having adhesiveness to bone and/or fascia which is useful as a medical material such as an artificial dura mater, and a process for producing the same.

BACKGROUND ART

Among three layers of membranes (pia mater, arachnoid, and dura mater) for protecting cerebral parenchyma in a cranial bone, the dura mater is the hardest outermost layer and is also the inner periosteum of the cranial bone. In brain neurosurgery, excision of the dura mater is often unavoidable, and this causes a defect in the dura mater. Spontaneous contraction of the dura mater itself sometimes complicates primary suturing. Occlusion of wound while the dura mater remains open results in serious complications, for example, intracranial infection caused by leakage of spinal fluid, local neurological symptom caused by adhesion between cerebral parenchyma and bones or subcutaneous tissues, and a focus of epileptic seizure. Therefore, when a wound is occluded, precise suturing is required in order not to create a gap in the dura mater. When a defect appears in the dura mater, or primary suturing is difficult, some prosthesis should be used to completely suture without any gap.

Selection of a prosthesis for use in filling a dura mater defect is a problem which has troubled neurosurgeons for a long time. At an early stage, artifacts were used, however, there were problems such as biocompatibility and usability. Thus, no artifact has been used for a long period. Autogenous fascia is the most extensively used prosthesis from the early stage up to the present, but problems associated with autoaenous fascia include production of fascia defect on the extracted region and easy adhesion to the brain. A human dried dura mater is a prosthesis for the dura mater prepared by treating the dura mater collected from a corpse with radiation, and has been the best prosthesis among existing ones. However, prions which may be a cause of Creutzfeldt Jakob disease, are potentially present in the dura mater, and infection of Creutzfeldt Jakob disease through a human dried dura mater has been reported. Therefore, use thereof was completely prohibited in 1998.

The only material usable as a prosthesis for the dura mater in addition to autogenous fascia is ePTFE (expanded polytetrafluoroethylene), which has been approved by Department of Health and Human Services. Because ePTFE is a polymeric material, it has no adhesiveness to organisms. This property is excellent in that ePTFE does not adhere to the brain. On the other hand, ePTFE is poor in contractility, and spinal fluid can leak from a pinhole, thereby requiring suturing with the use of special surgical suture. Since there is no adhesiveness to organisms, spinal fluid is highly likely to leak from a gap between suture surfaces. In addition, since there is no adhesiveness to peripheral tissue, it is highly likely to be no more than a skeletal material. Many attempts have been heretofore made on how to successfully use ePTFE. However, all of these attempts involved using ePTFE as a skeletal material and waiting until a coat of fibrous tissue was formed on the periphery.

SUMMARY OF THE INVENTION

The present inventors have heretofore conducted various experiments by modifying a surface layer of a polymeric material by the ion implantation technique and changing the cell adhesiveness, and have examined utility values thereof. The present inventors have aimed at development of a novel artificial dura mater with one side having no cell adhesiveness and the other side having cell adhesiveness, by means of surface modification of the polymeric material by the ion implantation technique.

When a polymeric material is irradiated with an ion beam, the admitted ion occasionally loses energy by collision with a matrix atom and finally stops. Over the course thereof, bond cleavage or new bonding occurs. In general, when nuclear stopping power is controlling, occurrence of defects such as radicals or change in conformation, density, and morphology, is observed. In contrast, when electron stopping power is controlling, electronic excitation ensures, and cleavage or crosslinking of a branched-Chain is thought to occur. Interatomic bonds of polymeric materials have a binding energy of about several eV, and the amount of energy per unit length to be applied to the matrix by ion beam irradiation is several tens of eV/Å. That is, it is the application of an energy flux ten times or larger than the binding energy. Change in physical property of polymeric materials by the irradiation of this energy flux has been observed. These phenomena vary depending on the type of ion beam, acceleration energy, amount of irradiation, and type of matrix. When polymeric materials are irradiated with an ion beam, beam current should not be excessively raised because polymeric materials have a low tolerance for beat. Also, since polymeric materials are electrical insulators. attention should be paid to the possibility that an accurate applied amount may not be measured by current measurement.

The present inventors have heretofore conducted surface modification by irradiating various polymeric materials with ion species such as helium (He) and neon (Ne), and have repeated basic experiments relating to cell adhesiveness by using a cultured cell system. As a result, it has been clarified that cell adhesiveness can be imparted by irradiation of Ne-ion beam at an acceleration energy of 150 keV and at an ion beam current of 0.5 $\mu$A/cm$^2$ or below to ePTFE, the application of which to human has been approved. Also, it has been clarified that cell adhesiveness varies depending on the amount of ion irradiation, and sufficient adhesiveness cannot be attained with an excessively large or small amount of irradiation. In hitherto experiments, cell adhesiveness was observed on the Ne-ion irradiated ePTFE surface at a dose of 1×10$^{14}$ ions/cm$^2$, and adhesiveness was the highest at a dose of around 1×10$^{15}$ cm$^2$ while cell adhesiveness was lowered at a dose of 1×10$^{17}$ ions/cm$^2$. Amorphous carbonization by ion beam irradiation was heretofore considered to enhance adhesiveness. However, cell adhesion was observed even at the dose of 1×10$^{14}$ ions/cm$^2$. The amount added at this dose is insignificant based on a theoretical calculation, and irradiation damage is at a level that cannot be detected by analysis such as Fourier transform infrared spectroscopy or Raman spectroscopy. Cells detect such a subtle change, and adhere. How cells detect this subtle change, and the mechanism of adhesion are not yet elucidated, and study thereof is being conducted using various analytical instruments.

Polymeric materials to which an ion beam has been applied show improvement in cell adhesiveness as well as adhesion strength. Cells allow substances similar to octopus legs referred to as "desmosomes" to invade onto a surface of the artificial material, thereby immobilizing themselves. It is predicted that adhesion strength on the ion beam irradiated surface is probably improved by increasing desmosomes. It has been confirmed that ion beam-irradiated polymeric materials has a smooth surface, so long as the region was observed under an atomic force microscope, and it is not because the surface is roughened due to ion beam irradiation and the adhesion area with cells enlarged, as initially predicted. It has been confirmed in a basic experiment using cultured cells that desmosomes are increased by selecting surface modification conditions.

By determining an optimal dose of ion beam to ePTFE, which is applicable to organisms, based on the data collected by hitherto basic experiments, clinical application can presumably be made possible. At an early stage, ePTFE, the surface of which has been treated at the optimal dose, only played a roll as an artificial dura mater for filling a defected portion on the dura mater in cranial neurosurgery. However, as considering the fact that the human dried dura mater has been used as a prosthesis used in skull base formation in skull base surgery, as a prosthesis in the surgical operation of spinal disease, and also as a prosthesis in other surgery on an abdominal or thoracic organ or musculoskeleton, the present inventors have come to consider the existence of a more extensive scope of application. In any site, if tissue adhesion is not desired on one side while tissue adhesion is desired on the other side, this Ne-ion beam-irradiated ePTFE can be widely used.

However, the above-mentioned data on cell adhesiveness of ePTFE is merely collected in vitro, i.e., in a cultured cell system. Thus, a degree of in vivo cell adhesiveness actually exhibited by Ne-ion beam-irradiated ePTFE has not been elucidated. Therefore, it is not clear whether or not the optimal ion beam dose of $1\times10^{15}$ ions/cm$^2$ that has been obtained in a cultured cell system is the optimal dose in vivo. There has been heretofore no report on types of morphological, histochemical conditions caused by cell adhesiveness that would occur in vivo, and in particular, on dynamics of desmosomes. Since a self-control system, that is, a tissue repair mechanism, is active in vivo, the occurrence of a situation is not hard to imagine which is unexplainable from a simple reaction such as in the cultured cell system. Also, there is a lot of unknown problems including the clinical significance of the reinforcement of cell adhesiveness that would actually occur in vivo, the problem of biocompatibility, the operability premising the surgical operation, and the occurrence of a reaction against foreign body.

Specifically, the object of the present invention is to elucidate the manner in which ePTFE adheres to cells together with morphological and histochemical changes over the period of time, by allowing ePTFE which has been irradiated with an ion beam under certain condition to closely adhere to bones and muscles, and also to examine whether or not this cell adhesiveness is enduring in the clinical application.

The present inventors have conducted concentrated studies in order to attain the above object, and as a result, they found that Ne-ion beam-irradiated ePTFE had cell adhesiveness even in vivo, thereby completing the present invention.

Thus, according to the present invention, there is provided a material having adhesiveness to bone and/or fascia, which is composed of a polymeric material comprising carbon as a constituent element, and at least a part of a surface of which is modified by ion bombardment.

According to a preferred embodiment of the present invention, there is provided the above-mentioned material wherein the polymeric material comprising carbon as a constituent element is expanded polytetrafluoroethylene (ePTFE), polylactic acid, or Polyglactin; and the above-mentioned material wherein modification by ion bombardment is performed by ion implantation in a dose $\phi$ range of $1\times10^{13} \leq \phi < 1\times10^{16}$ ions/cm$^2$.

According to another aspect of the present invention, there is provided a material for an artificial dura mater which is composed of the material having adhesiveness to bone and/or fascia as mentioned above.

According to further another aspect of the present invention, there is provided a process for producing a material having adhesiveness to bone and/or fascia wherein ion implantation is performed in a dose $\phi$ range of $1\times10^{13} \leq \phi < 1\times10^{16}$ ions/cm$^2$ on at least a part of a surface of a polymeric material comprising carbon as a constituent element.

According to a preferred embodiment of the present invention, there is provided the above-mentioned process wherein the polymeric material comprising carbon as a constituent element is expanded polytetrafluoroethylene (ePTFE), a polylactic acid, or Polyglactin.

BRIEF DESCRIPTION OF DRAWINGS

FIG. 1 shows morphological changes in ePTFE on fascia wherein:

FIG. 1-1: changes on muscle on the second week at a dose of $1\times10^{14}$ ions/cm$^2$; Adhesion is observed between a small number of histiocytes and fibroblasts on the irradiated surface, while no cell adhesion is observed at all on the unirradiated surface.

FIG. 1-2: changes on muscle on the fourth week at a dose of $1\times10^{14}$ ions/cm$^2$; Strong adhesion of fibroblasts and desmosomes are observed on the irradiated surface, while no cell adhesion is observed at all on the unirradiated surface.

FIG. 1-3: changes on muscle on the second week on an unirradiated surface; Accumulation of histiocytes is observed on the surface which is in contact with ePTFE, i.e., the outermost layer of the fibrous tissue, and FIG. 1-4 shows changes on muscle on the fourth week on the unirradiated surface. A solid coating of fibrous tissue is formed so as to cover ePTFE. Histiocytes still remain in the portion in contact with ePTFE.

FIG. 2 shows morphological changes in ePTFE on fascia and bones wherein

FIG. 2-1 shows changes on muscle on the second week at a dose of $5\times10^{14}$ ions/cm$^2$; Strong adhesion between histiocytes and fibrous tissues on the surface of ePTFE, a small number of desmosomes, and penetration of liquid component are observed.

FIG. 2-2 shows changes on muscle on the fourth week at a dose of $5\times10^{14}$ ions/cm$^2$; Strong fibrous adhesion is observed on ePTFE and the number of desmosomes is also increased.

FIG. 2-3 shows changes on bone on the second week at a dose of $1\times10^{14}$ ions/cm$^2$; ePTFE is in contact with bones, however, fibroblasts are present therebetween; and FIG. 2-4 shows changes on bone on the second week at a dose of $5\times10^{14}$ ions/cm$^2$; Strong fibrous adhesion, and desmosomes are present on ePTFE. Penetration of liquid component is also significant.

FIG. 3 shows morphological changes in ePTFE on fascia and bones wherein

FIG. 3-1 shows changes on muscle on the fourth week at a dose of $1\times10^{15}$ ions/cm$^2$; Significant level of penetration of liquid component and thick cell adhesion are observed. Expression of phagocytes is also observed.

FIG. 3-2 shows changes on muscle on the fourth week at a dose of $1\times10^{15}$ ions/cm$^2$; There is substantially no penetration of liquid component. Histiocytes were expressed on the surface of the muscular tissue, and solid cell adhesion is created.

FIG. 3-3 shows changes on bone on the second week at a dose of $1\times10^{15}$ ions/cm$^2$; Various cell components is adhered to ePTFE. Many desmosomes are observed, and penetration of liquid component is also significant, and FIG. 3-4 shows changes on bone on the fourth week at a dose of $1\times10^{14}$ ions/cm$^2$. Long desmosomes are observed on ePTFE, while penetration of liquid component is insignificant.

FIG. 4 shows morphological changes in ePTFE on bones wherein

FIG. 4-1 shows changes on bone on the fourth week at a dose of $5\times10^{14}$ ions/cm$^2$; Liquid component is penetrated into a considerably deep level. Long legs of desmosomes are observed along therewith.

FIG. 4-2 shows changes on bone on the fourth week at a dose of $1\times10^{15}$ ions/cm$^2$; Deep, wide, and accumulated desmosomes. Penetration of liquid component is significant.

FIG. 4-3 shows changes on bone on the second week at a dose of $1\times10^{15}$ ions/cm$^2$; The bone tissue is present in contact with ePTFE, and a small number of histiocytes and fibroblasts are present therebetween, and FIG. 4-4 shows changes on bone on the fourth week at a dose of $1\times10^{16}$ ions/cm$^2$. There are substantially no histiocytes or fibroblasts, and the bone tissue is in direct contact with ePTFE. Liquid component is not substantially penetrated, and existence of desmosomes is not clear.

EMBODIMENT FOR CARRYING OUT THE INVENTION

The embodiment for carrying out the present invention will be described below in detail.

Any material can be used without particular limitation as a polymeric material comprising carbon as a constituent element used in the present invention, so far as the material has biocompatibility and easy operability. Preferred polymeric materials used in the present invention include expanded polytetrafluoroethylene (ePTFE) and biodegradable polymers (for example, polylactic acid and Polyglactin). Expanded polytetrafluoroethylene (ePTFE) is particularly preferred.

At least a part of the surface of the polymeric material having adhesiveness to bones and/or muscles of the present invention is modified by ion bombardment. Examples of ionic species to be implanted include He$^+$, C$^+$, N$^+$, Ne$^+$, Na$^+$, N$_2^+$, O$_2^+$, Ar$^+$, and Kr$^+$, although the ionic species are not particularly limited to these unless the ionic species inhibit cell growth by elution.

The dose $\phi$ is preferably in the range of $1\times10^{13} \leq \phi < 1\times 10^{16}$ ions/cm$^2$. When the dose is lower than $10^{13}$ ions/cm$^2$, a significant improvement effect of cell adhesiveness is lowered. When the dose is higher than $10^{16}$ ions/cm$^2$, polymeric materials are likely to be damaged. Thus, neither thereof is preferred. The dose $\phi$ is more preferably in the range of $1\times10^{13} \leq \phi < 1\times10^{15}$ ions/cm$^2$.

Regarding the ion accelerating energy, its rise and fall may be causative of differences in the energy transfer mechanism. In practice, the energy level can be set in the range of about several tens to several hundreds keV, preferably about 50 to 150 keV.

The beam current density is preferably set in a range not exceeding approximately 0.5 $\mu$A/cm$^2$. This is because of a fear that an excessive beam current density excessively raises temperature of a target polymeric material, thereby deteriorating the polymeric material itself and lowering cell adhesiveness.

According to the present invention, means for imparting ion bombardment include ion implantation. In ion implantation, the reaction itself is limited to interaction between the ion beam and the material to be implanted (a target material). In addition, ions can be embedded at a desired depth from the surface by selecting ion implantation energy, and the controllability is excellent. This is a feature being absent in the plasma treatment. The implanted ions have mechanical differences, specifically, electron stopping power functions on ions having relatively low mass at the initial stage of diffusion, while nuclear stopping power functions on ions having relatively high mass from the outset. However, the implanted ions allow polymeric materials to be heated by lattice vibration (a state of thermal non-equilibrium), giving rise to melting, amorphization, and the like.

The present invention will be described in more detail with reference to the following examples although the present invention is not limited by these examples.

EXAMPLES (A) Summary of the Experiment (1) Correlation Between Organism Adhesiveness and Ion Dose of ePTFE having the Surface Modified by Ne-ion Beam-irradiation The results of hitherto experiments using a cultured cell system revealed that cell adhesiveness was attained at a dose of $1\times10^{14}$ ions/cm$^2$, the maximal cell adhesiveness was attained at a dose of $1\times10^{15}$ ions/cm$^2$, and cell adhesiveness was significantly lost at a dose of $1\times10^{16}$ ions/cm$^2$. In the in vivo implantation experiment, ePTFE at a dose of $1\times10^{15}$ ions/cm$^2$, ePTFE at a dose of $5\times10^{14}$ ions/cm$^2$, and ePTFE at a dose of $1\times10^{15}$ ions/cm$^2$ were used to observe and study variation of cell adhesiveness depending on the dose.

(2) Changes with Time in Organism Adhesion of ePTFE having the Surface Modified by Ne Beam Irradiation Cells are always acting dynamically in vivo, and an organism controlling system referred to as a mechanism of wound healing is operating. Therefore, even on the surface of the ion beam-irradiated surface-modified ePTFE, which has been implanted in the organism, cell adhesion would proceed with time. Observation for an ultra-short-term to an ultra-long-term is ideal, but it is difficult. Thus, observation of a specimen was concentrated and examined on the second week in which the primary adhesion of wound is approximately completed and the forth week in which a mechanism of repairing in tissue is presumably enhanced. Also in this case, since variation depending on the dose arises additionally, ePTFE at a dose of $1\times10^{14}$ ions/cm$^2$, ePTFE at a dose of $5\times10^{14}$ ions/cm$^2$, and ePTFE at a dose of $1\times10^{15}$ ions/cm$^2$, were respectively observed with time.

(3) Correlation of Adhesiveness between ePTFE having the Surface Modified by Ne Beam Irradiation and Different Tissues in Organisms One object of the present invention is to develop an artificial dura mater which, on filling a defect in the dura mater, has no cell adhesiveness on the surface contacting with the brain, but has cell adhesiveness on the surface contacting with cranial bone. However, when a human dried dura mater was used in the past, the human dried dura mater had been used in orthopedics, urological section, surgery and the like in addition to as a filling for the dura mater.

Thus, in order to confirm adhesiveness in other organs which is feasible in the same experiment system, an experiment for adhesion to rabbit muscles was also carried out.

(B) Method for Experiment (1) Sample

Three types of material were provided for use by irradiating 20 mm-square ePTFE having a thickness of 0.3 mm with Ne-ion at an acceleration energy of 150 keV, at the dose of $1\times10^{14}$ ions/cm$^2$, $5\times10^{14}$ ions/cm$^2$, and $1\times10^{15}$ ions/cm$^2$, respectively, at the ion beam current of 0.5 $\mu$A/cm$^2$ or below, using a 200 kV ion implantation apparatus (The Institute of Physical and Chemical Research). These three types of dose were selected based on the result of the basic experiment using a cultured cell system in which, cell adhesiveness to ePTFE was developed at the ion dose of $1\times10^{14}$ ions/cm$^2$, the adhesion effect became maximum at $1\times10^{15}$ ions/cm$^2$, and most of the adhesion effect was lost at $1\times10^{16}$ ions/cm$^2$. In the actual experiment, materials to be irradiated were cut to a size depending on the size of embedded portion in such a way that the material was unlikely to be influenced by ambient forces.

(2) Animal Test 10 male Japanese white rabbits weighing 2.5 to 3.0 kg were used in the experiment. Under general anesthesia with isoflurane, 2% xylocaine was locally injected, and the scalp was incised along the coronal suture to expose the cranial bone. With the periosteum on the surface of the cranial bone being completely removed, a sample was placed on the bone side with the irradiated surface facing the bone side. Since there is no muscular tissue on the bone, the possibility of the sample moving is very low and thus, immobilization was not particularly carried out. The reason why the periosteum was removed is that the artificial dura mater filled in the usual operation is in direct contact with bones having no periosteum since the dura mater is responsible for a part of the periosteum in the cranial bone.

Subsequently, 2% xylocaine was placed on the dorsal paramedian and skin was vertically incised under local anesthesia, and subcutaneous tissue was bluntly ablated to expose the back group of muscles. Fascia in the back group of muscles were carefully ablated so as not to damage muscles, a sample was placed so as to apply the irradiated surface on the muscular coat, and four corners were lightly sutured and immobilized on fascia. It is because, in portions in which muscles are present, a sample is highly likely to move accompanying the movement of the muscle.

(3) Observation

Two weeks and four weeks after the sample was embedded and implanted, rabbits were sacrificed using Nembutal, and peripheral tissue was respectively extracted as a mass, and immobilized with 10% buffer formalin. A peripheral tissue was extracted in order to avoid separation between ePTFE and a tissue, because tissue does not adhere to ePTFE on the surface which is not treated with the ion beam. The sample placed on the muscle was embedded in paraffin, while the sample placed on the cranial bone was embedded in paraffin after decalcification of cranial bone. The samples were stained by hematoxylin-eosin and by Masson's trichrome, and were observed under a microscope.

(C) Result (1) Morphological Change in ePTFE Placed on Fascia

As previously reported, cell adhesion was not observed at all on the untreated ePTFE surface on the second and fourth weeks (FIGS. 1-1 and 1-2 of FIG. 1). However, this does not indicate that there is no reaction at all in peripheral tissues. It seems that a smooth-surfaced fibrous tissue covers ePTFE interposing a narrow gap with ePTFE, on the second week, however, accumulation of histiocytes was observed on the surface of the fibrous tissue contacting ePTFE (FIG. 1-3 of FIG. 1). The present experiment could not clarify whether this accumulation developed as reactivity against ePTFE or a simple reaction of impaired tissue stump. On the fourth week, a fibrous component had increased in a histiocytes accumulated site, fibroblasts on the periphery had thickened, and a solid coating had formed (FIG. 1-4 of FIG. 1).

Figure 11:
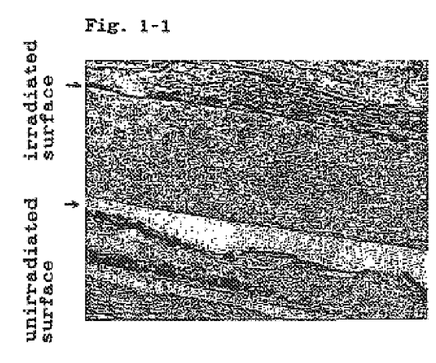
Figure 12:
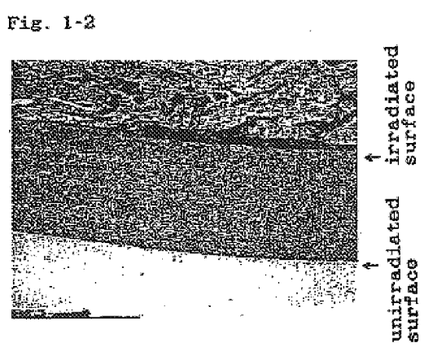
Figure 13:
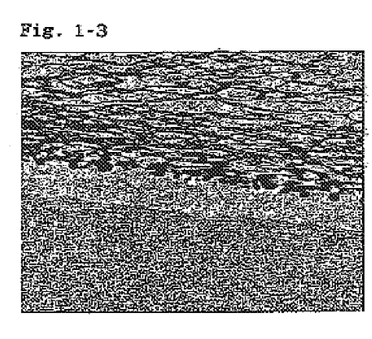
Figure 14:
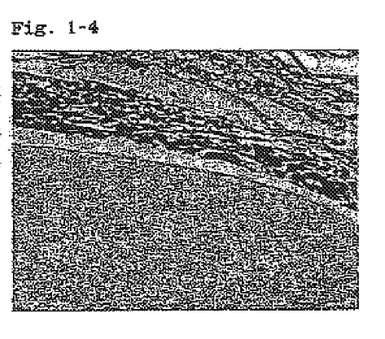
Figure 21:
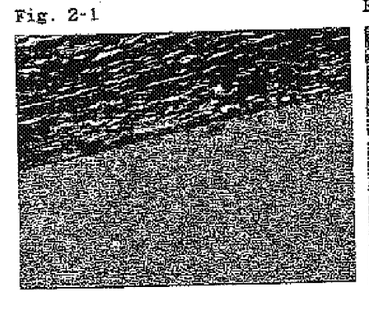

In contrast, adhesion of cells which were considered to be fibroblasts, was observed on the surface of a coating two weeks after implantation on the Ne-ion beam treated ePTFE surface, and cellular infiltration of histiocytes, lymphocyte or the like was observed inside the fibrous coating provided on the periphery (FIG. 2-1 of FIG. 2).

Figure 22:
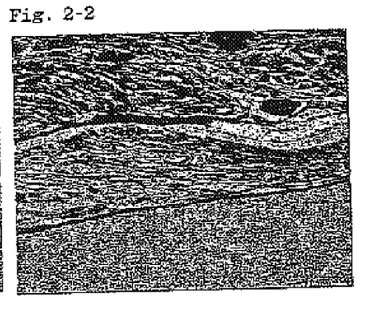

Penetration of liquid component into ePTFE was observed on the side of a treated surface. Such penetration of liquid component was not observed on the untreated surface. Penetrated liquid component presumably contains proteins from its stainability, although types of component actually penetrated are unclear and should be examined. Desmosomes, directly associated with adhesion strength between ePTFE and the adhered surface, were also observed, and exhibited a tendency in which desmosomes increased on the fourth week compared with the second week (FIG. 2-2 of FIG. 2).

Figure 31:
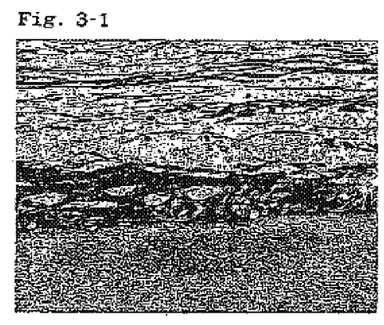
Figure 32:
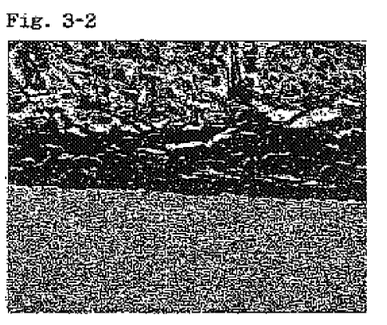

The accessibility between a fibroblast and an ion beam treated ePTFE surface was very low at $1\times10^{14}$ ions/cm$^2$, penetration of liquid component was little, and expression of desmosomes was also low. As the dose increased from $5\times10^{14}$ ions/cm$^2$ to $1\times10^{15}$ ions/cm$^2$, penetration of liquid component increased, and desmosomes tended to increase (FIG. 3-1 of FIG. 3). However, even though penetration of liquid component was not observed in some portions, there was a portion in which desmosomes were observed. Thus, penetration of liquid component and expression of desmosomes were not always in a parallel correlation (FIG. 3-2 of FIG. 3).

A similar finding was obtained from a specimen extracted on the fourth week. ePTFE irradiated at a dose of $1\times10^{14}$ ions/cm$^2$, exhibited adhesiveness equivalent to that at the second week, and the reactive fibrous component on the periphery had thickened. On ePTFE surfaces irradiated at $5\times10^{14}$ ions/cm$^2$ and at $1\times10^{15}$ ions/cm$^2$, cell adhesion had advanced compared with that at the second week, and desmosomes also tended to increase. Regarding the length of desmosomes, there was a portion exceeding 4000 Å, which was the offset of Ne-ion beam into ePTFE at 150 keV.

(2) Morphological Change in ePTFE Placed on the Cranial Bone

Figure 23:
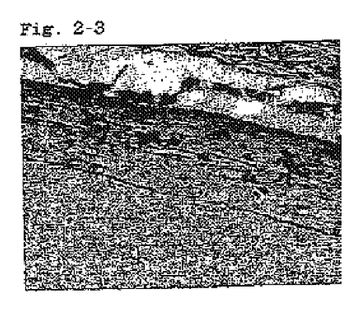
Figure 24:
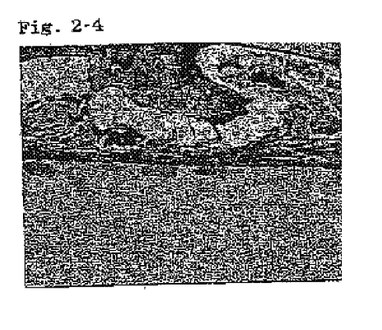
Figure 33:
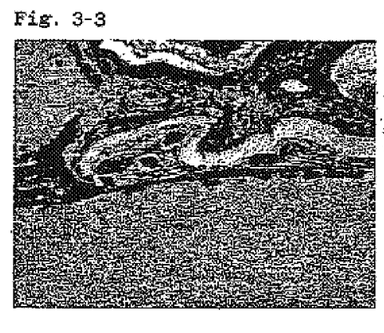
Figure 34:
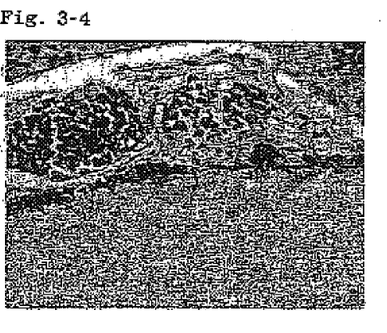
Figure 41:
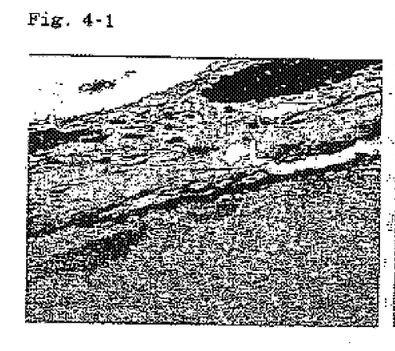
Figure 42:
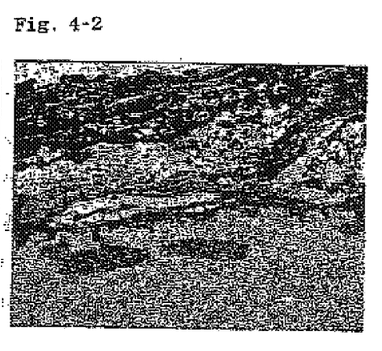
Figure 43:
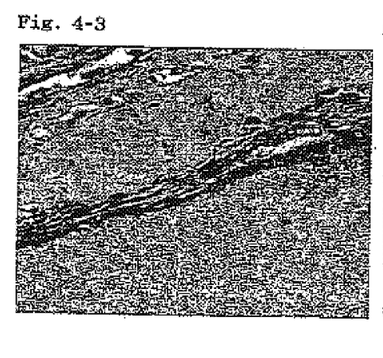
Figure 44:
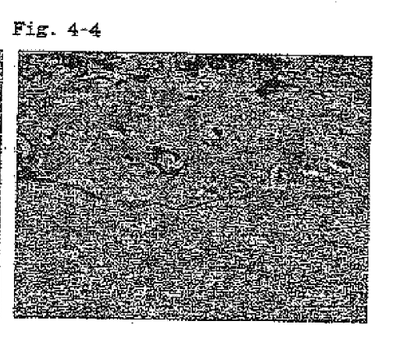

There was no difference in reaction on the untreated ePTFE surface from the case where ePTFE was placed on the fascia. Regarding the specimen extracted on the second week, cell adhesiveness was observed at $1\times10^{14}$ ions/cm$^2$ on the ion beam treated ePTFE surface that is in contact with bone, reaction of histiocytes and penetration of liquid component were observed, and a small number of desmosomes was also observed (FIG. 2-3 of FIG. 2). Compared with the case where ePTFE was placed on fascia, cell adhesion was impressively strong although it could not be objectively proved. As the dose increase from $5\times10^{14}$ ions/cm$^2$ to $1\times10^{15}$ ions/cm$^2$, contact of fibroblasts increased, and the reaction of histiocytes, penetration of liquid component and desmosomes tended to increase (FIG. 2-4 of FIG. 2, FIG. 3-3 of FIG. 3)

In the specimen extracted on the fourth week, although the group irradiated at $1\times10^{14}$ ions/cm$^2$ exhibited a tendency to increase the thickness of fibroblasts in contact, penetration of liquid component did not significantly increase (FIG. 3-4 of FIG. 3). Regarding groups irradiated at $5 \times 10^{14}$ ions/cm and $1 \times 10^{15}$ ions/cm$^2$, respectively, contact of fibroblasts on the ePTFE surface increased, and ePTFE desmosomes increased as with muscle surface, and accumulation of desmosomes was observed on a part (FIGS. 4-1 and 4-2 of FIG. 4). Penetration of liquid component was also considered to increase. On both the second and the fourth weeks, expression of histiocytes and fibroblasts was low and an image was observed in which an osteoblast-like tissue was in direct contact with ePTFE (FIGS. 4-3 and 4-4 of FIG. 4). However, it was not observed that this cell expressed desmosomes in ePTFE, and it could not be confirmed whether or not this was only simple contact.

The possibility was suggested that fibroblasts being in contact with an ion beam irradiated surface, produced desmosomes and invaded into ePTFE, and the distance exceeded the offset of the ion beam. This suggests that even if ePTFE does not have cell adhesiveness, there is a possibility for fibroblasts and the like to invade into ePTFE once the ePTFE grasps a chance. This also suggests a possibility of attaining a strong adhesiveness between ePTFE and cells advancing on the periphery.

(D) Conclusion and Discussion

A series of the present experiments clarified the following.

(1) Ne-ion beam-irradiated ePTFE has Cell Adhesiveness in vivo.

Experiments using a cultured cell system have demonstrated that Ne-ion beam-irradiated ePTFE has cell adhesiveness. Since a more complicated mechanism of wound healing actually exists in vivo, it was not clear how an organism reacted against Ne-ion beam-irradiated ePTFE. The present experiment have demonstrated that, in many cases, histiocytes, and in part, fibroblasts adhered to the treated surface on the second week regardless the amount of ion beam irradiated. In a small number of cases, it was observed that bone and muscle were in direct contact with bone and muscle without intermediating histiocytes or fibroblasts. Therefore, there are two possible cases in adhesion between a tissue and Ne-ion beam-irradiated ePTFE, i.e., a case where a cell adhesion factor, mainly consisting of histiocytes, plays a main role and a case where a peripheral tissue directly adheres.

(2) Cell Adhesiveness of Ne-ion beam-irradiated ePTFE in vivo Depends on the Amount of Ion Beam Irradiated.

It is reported that there is a clear correlation between cell adhesiveness to Ne-ion beam-irradiated ePTFE and the amount of ion beam irradiated in the cultured cell system. However, it was not clear whether or not this condition also holds true in vivo. A series of the present experiments demonstrated that, as with the cultured cell system, the ion beam irradiated ePTFE had cell adhesiveness in vivo and strongly adhered through desmosomes. In vivo, however, appearance of cells such as histiocytes or phagocyte, which are not observed in the cultured cell system, was suggested to have strong correlation with adhesiveness. Cell adhesiveness of Ne-ion beam-irradiated ePTFE was clearly increased as the dose increased from $1 \times 10^{14}$, $5 \times 10^{14}$ to $1 \times 10^{15}$, based on the condition of desmosome appearance and the like, as with the cultured cell system.

(3) Desmosomes Play a Key Role in Cell Adhesion to Ne-ion beam-irradiated ePTFE.

Observation of the adhered surface between Ne-ion beam-irradiated ePTFE and a peripheral tissue in the present experiment demonstrated four types of adhesion conditions: a) histiocytes adhered on the surface; b) fibroblasts adhered; c) bone and muscle existing on the periphery adhered; and d) desmosomes appeared from histiocytes and fibroblasts and adhered ePTFE as if putting legs into ePTFE. Although peel strength was not measured in each condition, strong adhesiveness cannot be expected from mere existence of histiocytes or fibroblasts on ePTFE. This is because a similar finding can be obtained even on the surface that is not treated with the ion beam. Since adhesion to ePTFE is not observed on the unirradiated surface, if histiocytes and fibroblasts seem to be merely resting on Ne-ion beam-irradiated ePTFE, small desmosomes are highly likely to be present.

(4) Liquid Component is Penetrated into Ne-ion beam-irradiated ePTFE.

Based on the present experiment, from the manner of coloring, it was found that a liquid component presumably containing proteins had penetrated into Ne-ion beam-irradiated ePTFE. There were sites where the liquid component had penetrated from the surface over a wide range, and sites where small fistula were present and the liquid component had penetrated from the surface to inside while exhibiting a large spread.

(5) Reaction on Ne-ion beam-irradiated ePTFE Adhered Surface is not Always in Parallel to the Amount of Ion Beam Irradiated, Tissue in Contact, and Reaction Time.

As a whole, a reaction on the adhered surface is enhanced at the optimal amount of irradiation, reinforced with the elapse of time, and develops a different reaction manner depending on the tissue in contact. However, when examining the experiment result in detail, conditions of histiocyte appearance on the adhered surface, conditions of fibroblast appearance, conditions of desmosome appearance and the like are not always in parallel to the amount of ion beam irradiation, the tissue in contact, reaction time and the like.

The result of the present in vivo implantation experiment using rabbits demonstrated sufficient cell adhesiveness, that is, Ne-ion beam-irradiated ePTFE exhibited a maximal effect at the dose of $1 \times 10^{15}$ ions/cm$^2$. Also, substantially equivalent adhesiveness was exhibited to bone and muscle. These results indicate that Ne-ion beam-irradiated ePTFE is applicable in various clinical fields as an artificial dura mater as a prosthesis for dura mater, as well as a prosthesis for organism membrane having a bilateral character of adhesiveness and nonadhesiveness.

Industrial Applicability

The present invention provides a novel artificial dura mater having cell adhesiveness and a process for producing the same. Specifically, the present invention realizes formation of the artificial dura mater having a function closer to that of an organism by imparting cell adhesiveness on the surface which is in contact with a cranial bone side. The present invention is further applicable as a prosthesis in surgery of spinal diseases and as a prosthesis in surgery on thoracic organs and abdominal organs or musculoskeleton in addition to the application thereof to the artificial dura mater.

The present disclosure relates to subject matter contained in priority Japanese Patent Application No. 2001-124294, filed on Apr. 23, 2001, the contents of which is herein expressly incorporated by reference in its entirety.

What is claimed is:

1. A material for an artificial dura mater which is composed of material having adhesiveness to at least one of bone or fascia, said material being composed of a polymeric material comprising carbon as a constituent element, and at least a part of a surface of the polymeric material is modified by ion bombardment.

2. A method for adhering a material having adhesiveness to at least one of bone or fascia comprising applying a polymeric material to at least one of bone or fascia, the polymeric material comprising carbon as a constituent element, and at least a part of a surface of the polymeric material is modified by ion bombardment so that the polymeric material has adhesiveness to at least one or bone or fascia.

3. The method according to claim 2 wherein the polymeric material comprising carbon as a constituent element is expanded polytetrafluoroethylene (ePTFE), polylactic acid, or glycolic-lactic acid polyester.

4. The method according to claim 2 wherein modification by ion bombardment is performed by ion implantation in a dose $\phi$ range of $1\times10^{13} \leq \phi < 1\times10^{16}$ ions/cm$^2$.

5. A method for filling a dura mater defect comprising applying a polymeric material to the dura mater defect, the polymeric material comprising carbon as a constituent element, and at least a part of a surface of the polymeric material is modified by ion bombardment.

6. The method according to claim 5 wherein the polymeric material comprising carbon as a constituent element is expanded polytetrafluoroethylene (ePTFE), polylactic acid, or glycolic-lactic acid polyester.

7. The method according to claim 5 wherein modification by ion bombardment is performed by ion implantation in a dose $\phi$ range of $1\times10^{13} \leq \phi < 1\times10^{16}$ ions/cm$^2$.

* * * * *

UNITED STATES PATENT AND TRADEMARK OFFICE
CERTIFICATE OF CORRECTION

PATENT NO.    : 6,872,759 B2
DATED         : March 29, 2005
INVENTOR(S)   : Y. Suzuki et al.

It is certified that error appears in the above-identified patent and that said Letters Patent is hereby corrected as shown below:

Column 11,
Line 7, "or" should be -- of --.

Signed and Sealed this

Fifteenth Day of November, 2005

JON W. DUDAS
*Director of the United States Patent and Trademark Office*